(12) United States Patent
Martelli

(10) Patent No.: US 10,166,134 B1
(45) Date of Patent: Jan. 1, 2019

(54) ADJUSTABLE, MULTI-AXIS STABILIZER APPARATUS AND METHOD

(71) Applicant: John D. Martelli, Pensacola, FL (US)

(72) Inventor: John D. Martelli, Pensacola, FL (US)

(*) Notice: Subject to any disclaimer, the term of this patent is extended or adjusted under 35 U.S.C. 154(b) by 338 days.

(21) Appl. No.: 14/958,963

(22) Filed: Dec. 4, 2015

(51) Int. Cl.
  *A61F 5/01* (2006.01)

(52) U.S. Cl.
  CPC ........ *A61F 5/01* (2013.01); *A61F 2005/0167* (2013.01)

(58) Field of Classification Search
  CPC ............ A61F 5/0102; A61F 2005/0167; A61F 5/0123; A61F 5/0125; A61F 2005/0139; A61F 5/0111; A61F 5/0585; A61F 5/0127; A61F 5/0195
  See application file for complete search history.

(56) References Cited

U.S. PATENT DOCUMENTS

| | | | | |
|---|---|---|---|---|
| 3,779,654 A | * | 12/1973 | Horne | A61F 2/582 403/62 |
| 5,086,760 A | * | 2/1992 | Neumann | A61F 5/0123 602/16 |
| 5,630,791 A | * | 5/1997 | Glynn | A61F 5/0125 602/16 |
| 6,203,511 B1 | * | 3/2001 | Johnson | A61F 5/0125 602/16 |
| 8,858,480 B1 | * | 10/2014 | Martelli | A61F 5/0125 602/16 |

* cited by examiner

*Primary Examiner* — Ophelia A Hawthorne
(74) *Attorney, Agent, or Firm* — J. Nevin Shaffer, Jr.

(57) ABSTRACT

An improved adjustable, multi-axis, motion stabilizer apparatus and method includes a first curved cup with a curved radius, the first curved cup with an inside surface and an outside surface. A cup hole extends through the first curved cup. A second curved cup is provided, also with a curved radius. The curved radius of the second curved cup is approximately equal to the curved radius of the first curved cup. The second cup also includes an inside surface and an outside surface where the outside surface of the second curved cup fits with the inside surface of the first curved cup. A cup hole is provided in the second curved cup and a pin, conformed to fit in the cup holes, connects the first curved cup with the second curved cup. A rotation slot is provided in the first curved cup and a limit boss is provided in the second curved cup where the limit boss is configured to fit within the rotation slot.

20 Claims, 5 Drawing Sheets

ADJUSTABLE, MULTI-AXIS STABILIZER APPARATUS AND METHOD

FIELD OF THE INVENTION

This invention relates to an improved adjustable, multi-axis motion stabilizer apparatus and method. In particular, in accordance with one embodiment, the invention relates to an improved adjustable, multi-axis, motion stabilizer apparatus including a first curved cup with a curved radius, the first curved cup with an inside surface and an outside surface. A cup hole extends through the first curved cup. A second curved cup is provided, also with a curved radius. The curved radius of the second curved cup is approximately equal to the curved radius of the first curved cup. The second cup also includes an inside surface and an outside surface where the outside surface of the second curved cup fits with the inside surface of the first curved cup. A cup hole is provided in the second curved cup and a pin, conformed to fit in the cup holes, connects the first curved cup with the second curved cup. A rotation slot is provided in the first curved cup and a limit boss is provided in the second curved cup where the limit boss is configured to fit within the rotation slot

BACKGROUND OF THE INVENTION

The present invention is an improvement on Applicant's U.S. Pat. No. 8,858,480 and is incorporated herein by reference. By way of example only and not by way of limitation, a problem exists with regard to rehabilitation after injury or surgery. When a person suffers a knee injury, again for example only, the accepted practice is to stabilize the joint while it heals. Motion of the joint is often completely prohibited for a period of time. Once motion is permitted, prior art devices limit motion in all directions except one, for example, front to back motion only. The range of this motion, by prior art devices, may be gradually increased but is, again, limited to one axis only. Initially, prior art devices, braces and the like, are well suited to helping a user recover gradually from the injury by permitting limited motion in only one direction. A problem has been identified by the Applicant, however, in that a joint in order to fully recover must be allowed to move in any normal direction. However, that motion must be controllable such that it is limited to begin with and adjustable as the joint and muscles recover strength.

Thus, there is a need in the art for a device that is capable of progressing in range of motion as healing of the joint progresses while still protecting against re-injury due to over extension during healing or after where the range of motion is controllable in all directions including front to back while allowing some motion in all directions.

It therefore is an object of this invention to provide an improved adjustable, multi-axis, motion stabilizer apparatus and method that can fully immobilize an appendage such as an arm, leg, or neck, for example only and not by way of limitation, and that can expand its range of motion gradually and in limited ranges in all directions, including front to back, as the joint heals and which can be used after recovery to allow a full range of motion within a safe injury free range. It is a further object to simplify the operation of the apparatus and increase its ease of operation at the same time.

SUMMARY OF THE INVENTION

Accordingly, the improved adjustable, multi-axis, motion stabilizer apparatus of the present invention, according to one embodiment, includes a first curved cup with a curved radius, the first curved cup with an inside surface and an outside surface. A cup hole extends through the first curved cup. A second curved cup is provided, also with a curved radius. The curved radius of the second curved cup is approximately equal to the curved radius of the first curved cup. The second cup also includes an inside surface and an outside surface where the outside surface of the second curved cup fits with the inside surface of the first curved cup. A cup hole is provided in the second curved cup and a pin, conformed to fit in the cup holes, connects the first curved cup with the second curved cup. A rotation slot is provided in the first curved cup and a limit boss is provided in the second curved cup where the limit boss is configured to fit within the rotation slot All terms used herein are given their common meaning in light of the description herein and in reference to the Figures as more fully set forth hereafter.

In another aspect of the invention, the rotation slot includes an outer edge and an inner edge and further the rotation slot includes at least one pin hole in the outer edge and at least one pin hole in the inner edge and further including a rotation slot pin where the rotation slot pin is conformed to connect the at least one outer edge pin hole with the at least one inner edge pin hole across the rotation slot.

In one aspect, the rotation slot includes more than one pin hole in the outer edge and more than one pin hole in the inner edge. In a further aspect, the invention includes more than one rotation slot pin. In another aspect, the limit boss has a width and the more than one pin holes are spaced apart by at least the width of the limit boss.

In another aspect, the invention includes a size adjustment device connected with the cup holes for controlling movement of the cup pin within the cup holes. In one aspect, the size adjustment device is a bushing with a center hole where the center hole of the bushing is conformed to receive the shaft of the cup pin and where the bushing fits within at least one of the cup holes. In a further aspect, the bushing is of a certain dimension where the certain dimension is selected from a group of dimensions consisting of: the same dimension as at least one of the cup holes and a smaller dimension than at least one of the cup holes.

In one aspect, the invention includes a rotation plate connected with the cup pin. In a further aspect, the rotation plate is connected with the cup pin beneath the cup cap and above the outside surface of the first curved cup.

According to another embodiment, an improved adjustable, multi-axis, motion stabilizer apparatus includes a first curved cup with a curved radius, the first curved cup with an inside surface and an outside surface. A first cup hole is provided through the first curved cup. A second curved cup is provided with a curved radius where the curved radius of the second curved cup is approximately equal to the curved radius of the first curved cup, the second cup with an inside surface and an outside surface where the outside surface of the second curved cup fits with the inside surface of the first curved cup. A second cup hole in the second curved cup where the second cup hole is smaller than the first cup hole. A cup pin conformed to pass through the first cup hole and connect with the second cup hole and connect the first curved cup with the second curved cup where the cup pin includes a cap and a shaft. A size adjustment device for controlling movement of the cup pin within the first cup hole. A rotation slot in the first curved cup where the rotation slot includes an outer curved edge and an inner curved edge and further where the rotation slot includes at least one rotation slot pin hole in the outer curved edge aligned with at least one rotation slot pin hole in the inner curved edge and further including a rotation slot pin where the rotation slot pin is conformed to connect the at least one outer curved edge rotation slot pin hole with the at least one inner curved edge rotation slot pin hole across the rotation slot. And a limit boss in the second curved cup where the limit boss is configured to fit within the rotation slot.

In one aspect, the rotation slot includes more than one pin hole in the outer curved edge aligned with more than one rotation slot pin hole in the inner curved edge and further including more than one rotation slot pin.

In another aspect, the size adjustment device is a bushing with a center hole where the center hole of the bushing is conformed to receive the shaft of the cup pin and where the bushing fits within the first cup hole. In a further aspect, the bushing is of a certain dimension where the certain dimension is selected from a group of dimensions consisting of: the same dimension as the first cup hole and a smaller dimension than the first cup hole.

In one aspect, the invention further includes a rotation plate connected with the first curved cup. In a further aspect, the rotation plate includes at least one ball bearing and is connected with the cup pin beneath the cup cap and above the outside surface of the first curved cup.

According to another embodiment, an improved adjustable, multi-axis, motion stabilizer method consists of:

a. providing a first curved cup with a curved radius, the first curved cup with an inside surface and an outside surface; a cup hole through the first curved cup; a second curved cup with a curved radius where the curved radius of the second curved cup is approximately equal to the curved radius of the first curved cup, the second cup with an inside surface and an outside surface where the outside surface of the second curved cup fits with the inside surface of the first curved cup; a cup hole in the second curved cup; a cup pin conformed to fit with the cup holes and connect the first curved cup with the second curved cup where the cup pin includes a cap and a shaft; a rotation slot in the first curved cup and a limit boss in the second curved cup where the limit boss is configured to fit within the rotation slot; and b. connecting the first cup and the second cup to form a first unit and connecting the first unit with a user appendage.

In one aspect, the rotation slot includes an outer edge and an inner edge and further where the rotation slot includes at least one pin hole in the outer edge and at least one pin hole in the inner edge and further including a rotation slot pin where the rotation slot pin is conformed to connect the at least one outer edge pin hole with the at least one inner edge pin hole across the rotation slot.

In another aspect, the invention further includes a size adjustment device for controlling movement of the cup pin within the cup holes where the size adjustment device is a bushing with a center hole where the center hole of the bushing is conformed to receive the shaft of the cup pin and where the bushing fits within at least one of the cup holes and where the bushing is of a certain dimension where the certain dimension is selected from a group of dimensions consisting of: the same dimension as at least one of the cup holes and a smaller dimension than at least one of the cup holes.

In a further aspect, the invention further includes a rotation plate where the rotation plate is connected with the cup pin beneath the cup cap and above the outside surface of the first curved cup.

DESCRIPTION OF THE DRAWINGS

Other objects, features and advantages of the present invention will become more fully apparent from the following detailed description of the preferred embodiment, the appended claims and the accompanying drawings in which:

DETAILED DESCRIPTION OF THE INVENTION

Figure 1:
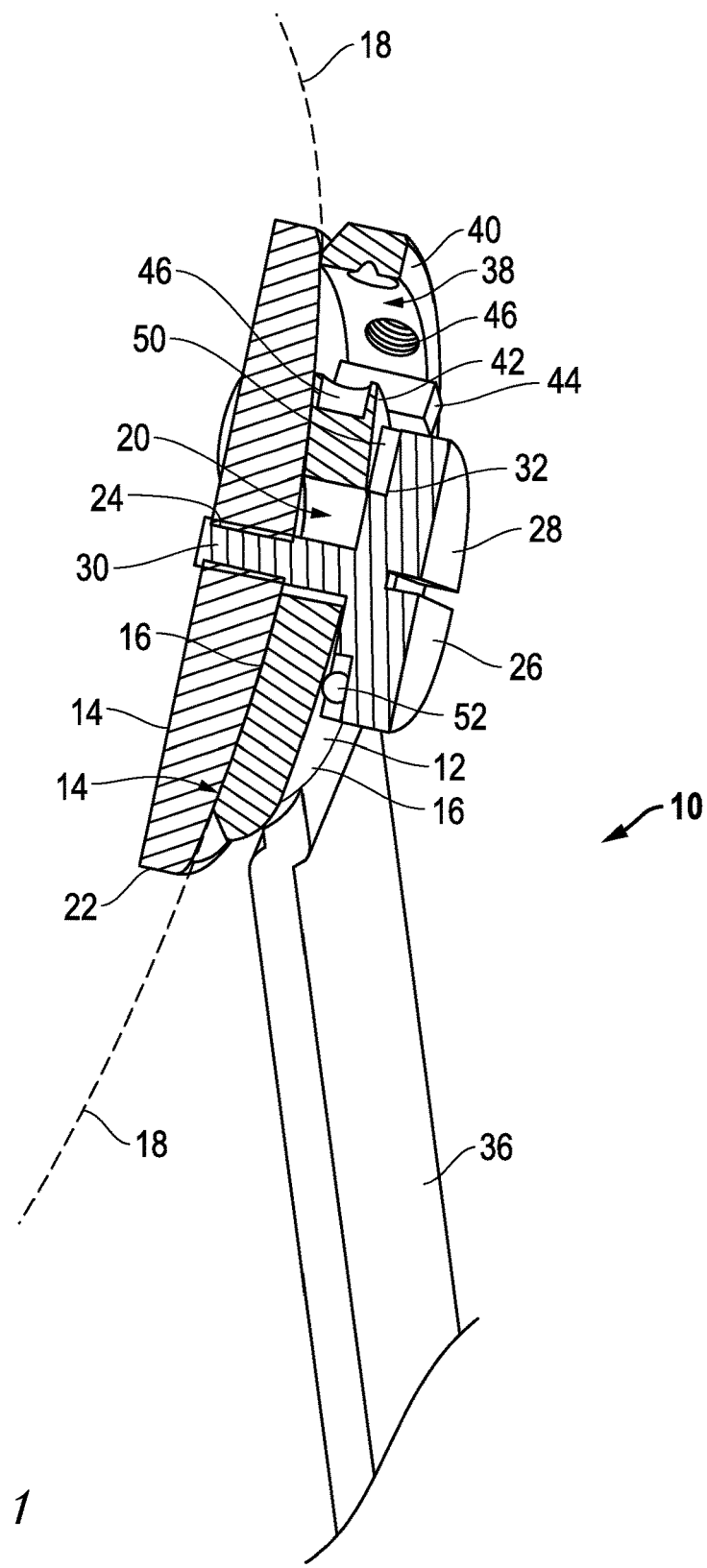
FIG. 1 is side partial cut away view of one embodiment of the improved adjustable, multi-axis, motion stabilizer apparatus showing the inside surfaces of the curved cups and a pin with a shoulder, the rotation slot, limit boss and rotation plate.

Before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the invention be regarded as including equivalent constructions to those described herein insofar as they do not depart from the spirit and scope of the present invention.

For example, the specific sequence of the described method may be altered so that certain processes are conducted in parallel or independent, with other processes, to the extent that the processes are not dependent upon each other. Thus, the specific order of steps described herein is not to be considered implying a specific sequence of steps to perform the process. In alternative embodiments, one or more process steps may be implemented by a user assisted process and/or manually. Other alterations or modifications of the above processes are also contemplated.

In addition, features illustrated or described as part of one embodiment can be used on other embodiments to yield a still further embodiment. Additionally, certain features may be interchanged with similar devices or features not mentioned yet which perform the same or similar functions. It is therefore intended that such modifications and variations are included within the totality of the present invention.

It should also be noted that a plurality of hardware devices, as well as a plurality of different structural components, may be utilized to implement the invention. Furthermore, and as described in subsequent paragraphs, the specific configurations illustrated in the drawings are intended to exemplify embodiments of the invention and that other alternative configurations are possible.

The preferred embodiment of the present invention is illustrated by way of example in FIGS. 1-5. With specific reference to FIGS. 1 and 2, an improved adjustable, multi-axis motion stabilizer apparatus 10 includes a first curved cup 12. As shown, first curved cup 12 is formed in a curved shape and includes an inside surface 14 and an outside surface 16. The inside surface 14 and the outside surface 16 are connected to form a first curved cup along a curved radius 18 (shown in a dotted line). As used herein, the term "curved radius" is given its common meaning. It should be understood that it represents a certain curvature and length. The length and curvature combine to create a particular curve. The Applicant has determined that a preferred curved radius 18 is approximately equal to one-half of the diameter of a user's appendage, such as a knee, for example only. By matching the curved radius 18 to the diameter of the user's appendage, smooth operation of the improved adjustable, multi-axis, motion stabilizer 10 is enabled, as will be more fully described hereafter. First cup hole 20 extends through first curved cup 12.

Second curved cup 22 includes a curved radius 18 that is approximately equal to the curved radius 18 of first curved cup 12. Second curved cup 22 also includes an inside surface 14 and an outside surface 16. The inside surface 14 and the outside surface 16 are connected to form second curved cup 22 along a curved radius 18 (shown in a dotted line). Thus, the outside surface 16 of the second curved cup 22 fits with the inside surface 14 of the first curved cup 12.

Figure 2:
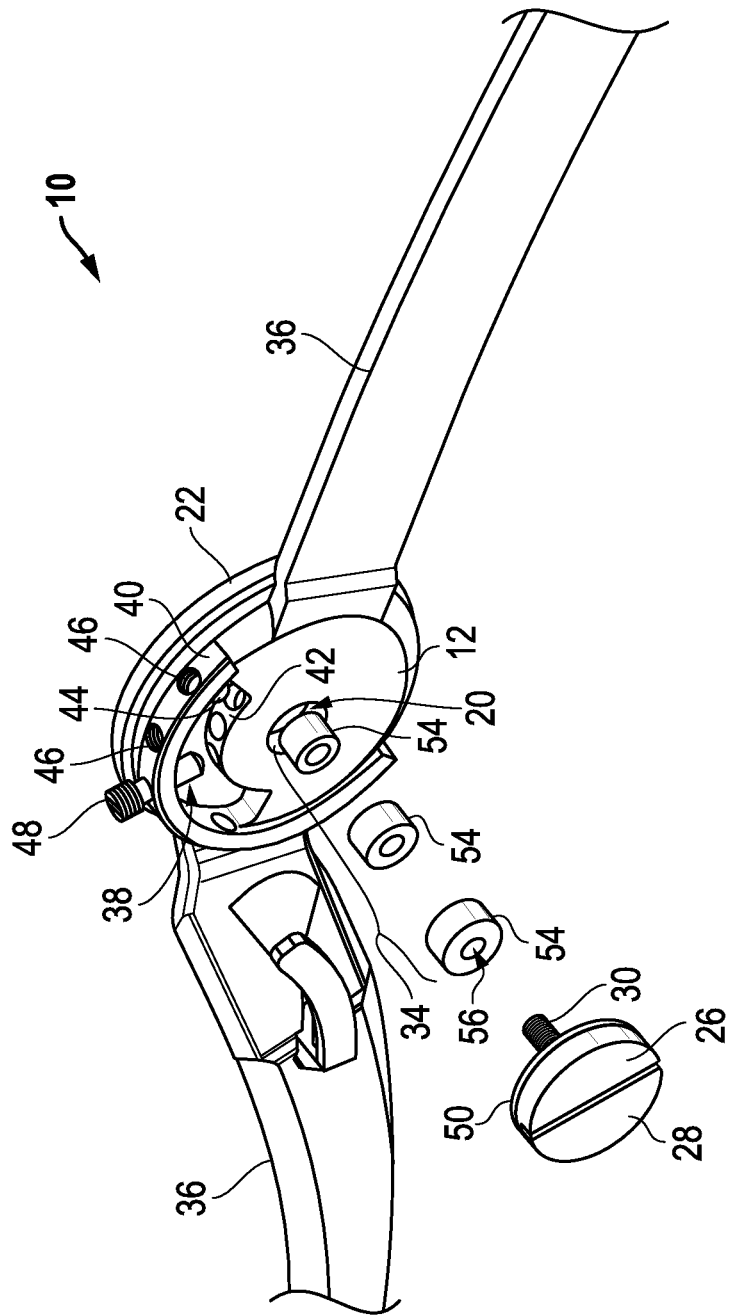
FIG. 2 is a side perspective view of the invention of FIG. 1 showing the rotation slot, multiple pin holes, limit boss, and multiple size adjustment devices of different diameter.

Still referring to FIGS. 1 and 2, second curved cup 22 includes a second cup hole 24. Second cup hole 24 may or may not extend all the way through second curved cup 22. Cup pin 26 includes, in one embodiment, a cap 28 and a threaded shaft 30. Threaded shaft 30 may or may not include a shoulder 32. Shoulder 32 is an expanded area of threaded shaft 30. Second cup hole 24 in second cup 22 receives the threaded shaft 30 and connects second curved cup 22 with first curved cup 12. Threaded shaft 30 does not engage first cup hole 20 of first curved cup 12. In practice, threaded shaft 30 may only include threads (not shown) on the portion of the shaft that engages second curved cup 22 leaving the rest of the shaft unthreaded and smooth. In any case, first curved cup 12 freely moves around threaded shaft 30 in one direction, front to back for example, and without bushings, as will be described more fully hereafter, in multiple axis ranges.

A size adjustment device 34 for controlling movement of the pin 26 threaded shaft 30 within first cup hole 20 will be described more fully with regard to FIGS. 3 and 4. Nonetheless, it should be understood that size adjustment device 34 enables limited motion in one direction when it approximately matches the size of first cup hole 20. When the size adjustment device 34 is smaller than first cup hole 20, then shaft 30 is free to move in any direction up to the limit of the size adjustment device 34 within first cup hole 20. In this case, motion, but controlled limited motion, is allowed in any direction or along any axis.

Still referring to FIGS. 1 and 2, extension(s) 36 are shown. In the embodiment where extensions 36 are present, one extension 36 is connected with first curved cup 12 and one extension 36 may also be connected with second curved cup 22. Extensions 36 enable the combined first curved cup 12 and second curved cup 22 to be held in place where desired, such as next to a user's knee, for example only. A wrap of some sort (not shown), such as a stretchable bandage can be wrapped around the extensions 36 both above and below the knee, for example, and hold the improved adjustable, multi-axis motion stabilizer 10 in place.

FIGS. 1 and 2 also illustrate rotation slot 38 in said first curved cup 12. Rotation slot 38 includes an outer edge 40 and an inner edge 42. Thus, rotation slot 38 is an empty space in first curved cup 12 from side to side and completely through first curved cup 12. The rotation slot 38 is formed in any shape desired and the remaining structure of first curved cup 12, the outer edge 40 and inner edge 42, is integral to the structure of first curved cup 12. A limit boss 44 fits within rotation slot 38. Preferably, limit boss 44 is attached and connected to second curved cup 22 on the outside surface 16 of second curved cup 22 as shown. Limit boss 44 fits within and is contained within rotation slot 38 when first curved cup 12 and second curved cup 22 are joined together as shown. By this novel means, the front to back movement of the improved adjustable, multi-axis stabilizer 10 is controlled and limited as desired.

Additionally, preferably, rotation slot 38 includes at least one pin hole 46 in the outer edge 40 and at least one pin hole 46 in the inner edge 42. In such a case, a rotation slot pin or pins 48 (as shown in FIGS. 3, 4 and 5) is/are provided. Rotation slot pin(s) 48 is/are conformed to connect the at least one outer edge pin hole 46 with the at least one inner edge pin hole 46 across the rotation slot 38. As used herein, the term "connect" is used to describe that the rotation slot pin 48 creates a transverse barrier across the rotation slot 38. Thus, as will be described more fully hereafter, by use of the rotation slot pin(s) 48, the travel of limit boss 44 within rotation slot 38 may be even more finely controlled.

Still referring to FIGS. 1 and 2, a rotation plate 50 is shown. Rotation plate 50 is conformed to facilitate movement between first curved cup 12 and second curved cup 22. Thus, preferably, rotation plate 50 includes ball bearing(s) 52 that connect with the first curved cup 12. As illustrated, rotation plate 50 is located beneath the cap 28 of cup pin 26 and on top of the outside surface 16 of first curved cup 12. Certainly, other locations, for example only and not by limitation, include on the outside surface 16 of second curved cup 22 and on the inside surface 14 of first curved cup 12, i.e. between the two curved cups, if deemed useful. Also, rotation plate 50 may be made of any slippery, non-stick substance now known or hereafter developed such that ball bearings 52 are not required.

Figure 3:
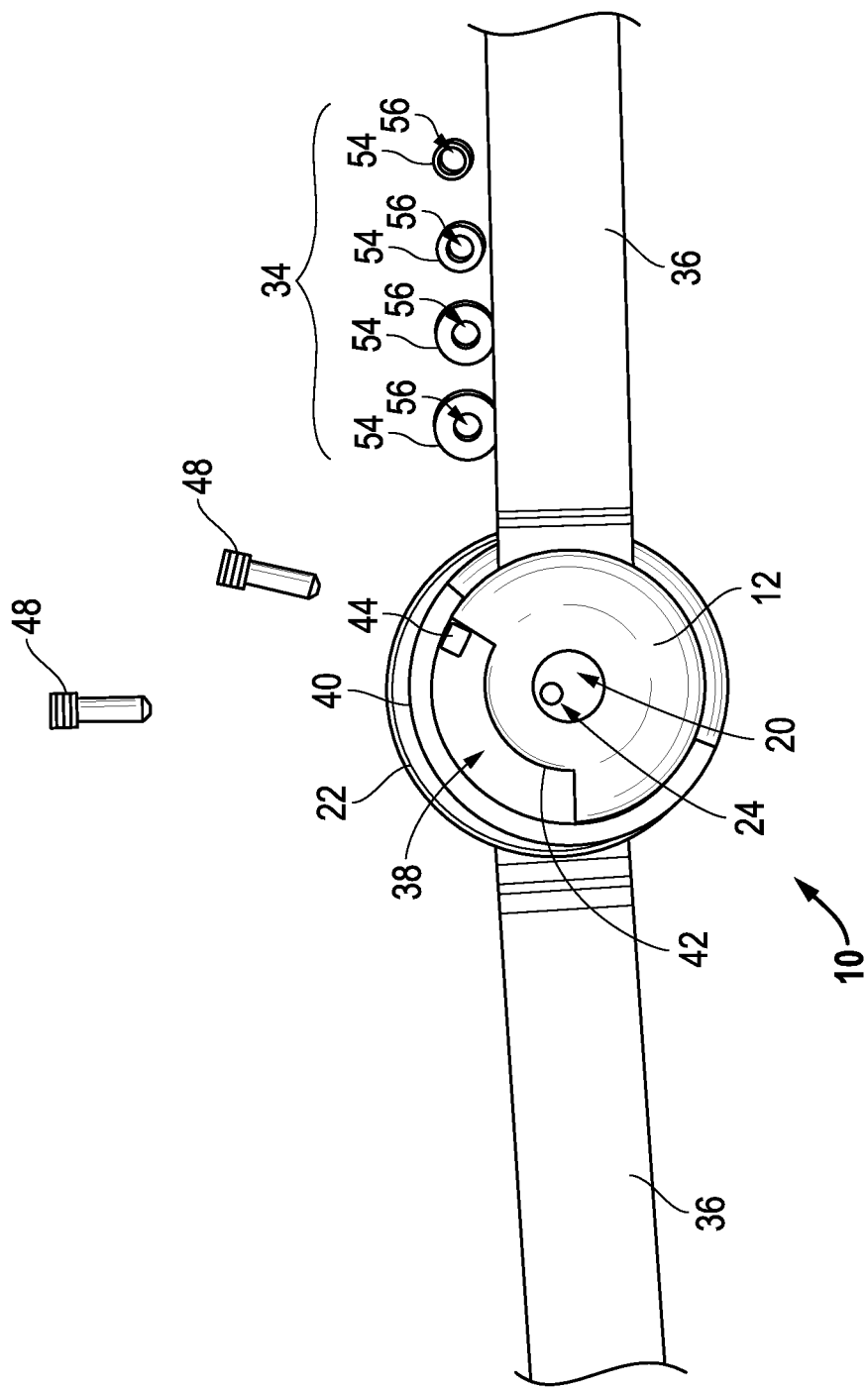
FIG. 3 is a top view of the invention of FIG. 1 without the cup pin showing the improved adjustable, multi-axis, motion stabilizer apparatus in the unbent position with multiple rotation slot pins and a range of different width bushings.
Figure 4:
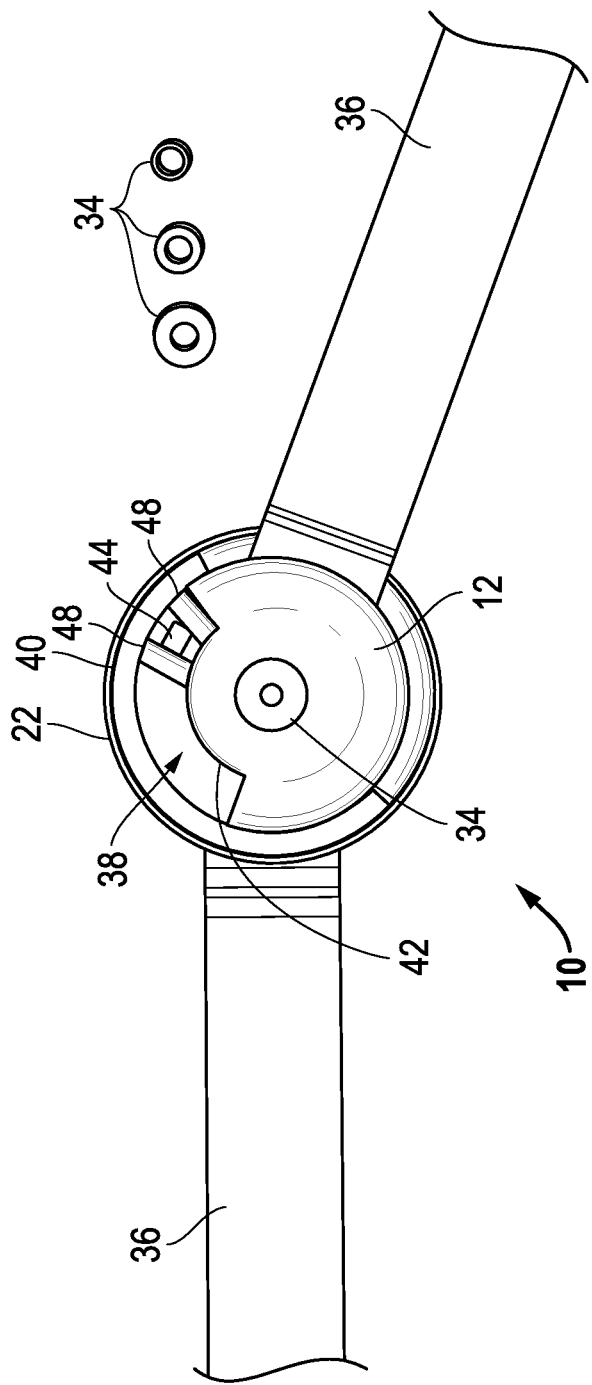
FIG. 4 is a top view of FIG. 3 with the improved adjustable, multi-axis, motion stabilizer apparatus bent and held in place by two rotation slot pins and with a bushing matching the size of the cup hole so as to prevent any motion.
Figure 5:
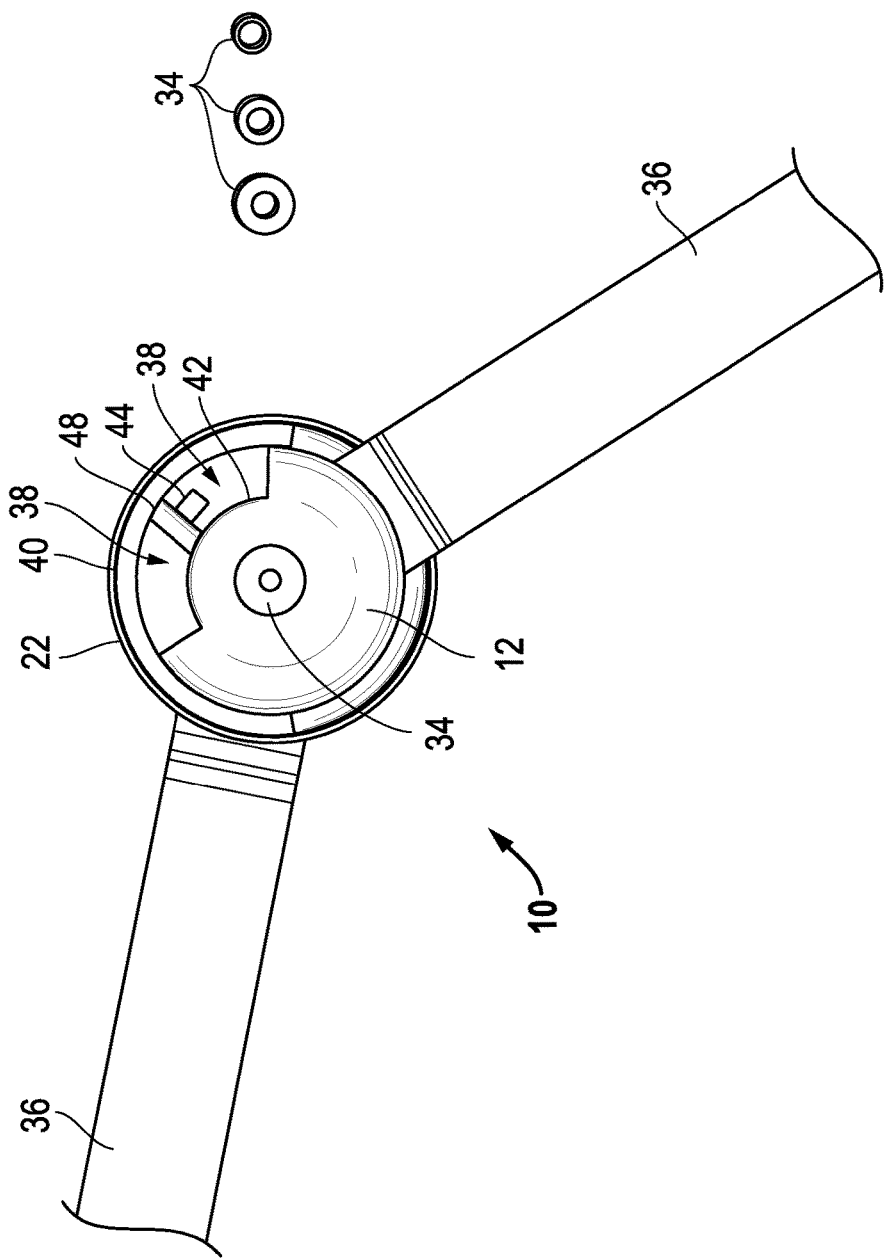
FIG. 5 is a top view of FIG. 3 with the improved adjustable, multi-axis, motion stabilizer apparatus bent with one rotation slot pin in place so as to allow limited front to back motion and with no bushing so that at the same time motion in any axis is permitted.

Referring now to FIGS. 3, 4 and 5, the use and structure of the features of improved adjustable, multi-axis motion stabilizer 10 are further illustrated and described. In FIG. 3, a top partial section view shows the first curved cup 12 with rotation slot 38 formed by outer edge 40 and inner edge 42 and with limit boss 44 from second curved cup 22 located within rotation slot 38. Thus, in this configuration, limit boss 44 is free to travel throughout all of the rotation slot 38.

FIG. 3 also shows rotation slot pins 48 and size adjustment devices 34. Importantly, preferably, size adjustment device(s) 34 are bushings 54. Bushings 54 have a center hole 56 that is conformed to movably receive threaded shaft 30 of cup pin 26 (not shown). By "movably receive" it is meant that threaded shaft 30 fits within center hole 56 just enough to do so without appreciable restriction of movement but not so much as to wobble. Bushings 54, while having the same dimension center hole 56, have a different dimension overall width as illustrated. The width of the bushings 54 are varied from large to small such that the largest bushing 54 just fits within first cup hole 20 (See FIG. 4) such that movement is limited simply to back and forth movement of the limit boss within rotation slot 38. FIG. 3 shows no bushing 54 in first cup hole 20 and, thus, improved adjustable, multi-axis stabilizer 10 is free to move along any axis as well as front to back within the limits of rotation slot 38.

An advantage of the present invention is that by use of the bushings 54 a single cup pin 26 with a single sized shaft 30 accommodates all bushings 54 and the bushings are held in place within first cup hole 20 by cap 26. This simplifies the procedure in the prior art patent and greatly decreases the chance of the size adjustment device 34 disconnecting.

FIG. 4, shows the largest width bushing 54 completely filling first cup hole 20 thereby preventing multi-axis movement. Additionally, FIG. 4 illustrates the use of two rotation slot pins 48 to trap limit boss 44 in place within rotation slot 38. This configuration keeps the users' appendage, for example, in a fixed location as at the beginning of a recovery.

FIG. 5 illustrates the use of the present invention to control front to back movement and allow multi-axis movement at the same time by use of a single rotation slot pin 48 and by not using a size adjustment device 34, bushing 54.

It should be clear by now, that the improved adjustable, multi-axis, stabilizer 10 of the present invention is capable of enabling and controlling a wide variety of movement from complete immobilization to controlled but full range motion in multiple axis as well as well as at the same time controlling front to back motion, a totally unique and useful improvement in the art.

It should also be understood that the present invention is extraordinarily well suited for use as an injury preventive device. No prior art device restricts motion of a joint beyond an acceptable point while enabling motion in all directions at the same time. Applicant's improved adjustable, multi-axis motion stabilizer 10 is adjustable to predetermined maximum degrees of motion in multiple directions, including front to back at the same time, thus providing protection against injury while enabling natural freedom of movement required for the activity.

The description of the present embodiments of the invention has been presented for purposes of illustration, but is not intended to be exhaustive or to limit the invention to the form disclosed. Many modifications and variations will be apparent to those of ordinary skill in the art. As such, while the present invention has been disclosed in connection with an embodiment thereof, it should be understood that other embodiments may fall within the spirit and scope of the invention as defined by the following claims.

What is claimed is:

1. An improved adjustable, multi-axis, motion stabilizer apparatus comprising:
   a. a first curved cup with a curved radius, the first curved cup with an inside surface and an outside surface;
   b. a cup hole through said first curved cup;
   c. a second curved cup with a curved radius wherein said curved radius of said second curved cup is approximately equal to the curved radius of said first curved cup, the second cup with an inside surface and an outside surface wherein said outside surface of said second curved cup fits with the inside surface of said first curved cup;
   d. a cup hole in said second curved cup;
   e. a cup pin conformed to fit with said cup holes and connect said first curved cup with said second curved cup wherein said cup pin includes a cap and a shaft;
   f. a rotation slot in said first curved cup; wherein said rotation slot includes an outer edge and an inner edge with the rotation slot formed thereby in between and further wherein said rotation slot includes at least one pin hole in said outer edge and at least one pin hole in said inner edge;
   g. a limit boss in said second curved cup wherein said limit boss is configured to fit within said rotation slot; and
   h. a rotation slot pin wherein said rotation slot pin is configured to fit within said at least one outer edge pin hole and connect said at least one outer edge pin hole with said at least one inner edge pin hole across said rotation slot and restrict movement of said limit boss within said rotation slot.

2. The apparatus of claim 1 further including a rotation plate connected with said cup pin.

3. The apparatus of the claim 2 wherein said rotation plate is connected with said cup pin beneath said cup cap and above the outside surface of said first curved cup.

4. The apparatus of claim 3 further including a rotation plate connected with said first curved cup.

5. The apparatus of the claim 4 wherein said rotation plate includes at least one ball bearing and is connected with said cup pin beneath said cup cap and above the outside surface of said first curved cup.

6. The apparatus of claim 1 wherein said rotation slot includes more than one pin hole in said outer edge and more than one pin hole in said inner edge.

7. The apparatus of claim 6 further including more than one rotation slot pin.

8. The apparatus of claim 6 wherein said limit boss has a width and wherein said more than one pin holes are spaced apart by at least the width of the limit boss.

9. The apparatus of claim 1 further including a size adjustment device connected with said cup pin within said cup holes wherein said size adjustment device allows one of said curved cups to move around said cup pin along multiple axis and front to back.

10. The apparatus of claim 9 wherein said size adjustment device is a bushing with a center hole wherein said center hole of said bushing is conformed to receive the shaft of said cup pin and wherein said bushing fits within at least one of said cup holes.

11. The apparatus of claim 10, wherein said bushing is of a certain dimension wherein said certain dimension is selected from a group of dimensions consisting of: the same dimension as at least one of said cup holes and a smaller dimension than at least one of said cup holes.

12. The apparatus of claim 1 wherein two rotation slot pins are provided such that when connected across said rotation slot said two rotation slot pins are located on opposite sides of said limit boss.

13. An improved adjustable, multi-axis, motion stabilizer apparatus comprising:
   a. a first curved cup with a curved radius, the first curved cup with an inside surface and an outside surface;
   b. a first cup hole through said first curved cup;
   c. a second curved cup with a curved radius wherein said curved radius of said second curved cup is approximately equal to the curved radius of said first curved cup, the second cup with an inside surface and an outside surface wherein said outside surface of said second curved cup fits with the inside surface of said first curved cup;
   d. a second cup hole in said second curved cup wherein said second cup hole is smaller than said first cup hole;
   e. a cup pin conformed to pass through said first cup hole and connect with said second cup hole and connect said first curved cup with said second curved cup wherein said cup pin includes a cap and a shaft;
f. a size adjustment device wherein said size adjustment device allows said first curved cup to move around said cup in along multiple axis and front to back;
g. a rotation slot in said first curved cup wherein said rotation slot includes an outer curved edge and an inner curved edge and further wherein said rotation slot includes at least one rotation slot pin hole in said outer curved edge aligned with at least one rotation slot pin hole in said inner curved edge and further including a rotation slot pin wherein said rotation slot pin is conformed to connect said at least one outer curved edge rotation slot pin hole with said at least one inner curved edge rotation slot pin hole across said rotation slot; and
h. a limit boss in said second curved cup wherein said limit boss is configured to fit within said rotation slot and wherein said at least one rotation slot pin limits movement of said limit boss in said rotation slot.

14. The apparatus of claim 13, wherein said rotation slot includes more than one pin hole in said outer curved edge aligned with more than one rotation slot pin hole in said inner curved edge and further including more than one rotation slot pin.

15. The apparatus of claim 13 wherein said size adjustment device is a bushing with a center hole wherein said center hole of said bushing is conformed to receive the shaft of said cup pin and wherein said bushing fits within said first cup hole.

16. The apparatus of claim 15 wherein said bushing is of a certain dimension wherein said certain dimension is selected from a group of dimensions consisting of: the same dimension as said first cup hole and a smaller dimension than said first cup hole.

17. The apparatus of claim 13 wherein two rotation slot pins are provided such that when connected across said rotation slot said two rotation slot pins are located on opposite sides of said limit boss.

18. An improved adjustable, multi-axis, motion stabilizer method comprising:
a. providing a first curved cup with a curved radius, the first curved cup with an inside surface and an outside surface; a cup hole through said first curved cup; a second curved cup with a curved radius wherein said curved radius of said second curved cup is approximately equal to the curved radius of said first curved cup, the second cup with an inside surface and an outside surface wherein said outside surface of said second curved cup fits with the inside surface of said first curved cup; a cup hole in said second curved cup; a cup pin conformed to fit with said cup holes and connect said first curved cup with said second curved cup wherein said cup pin includes a cap and a shaft; a rotation slot in said first curved cup wherein said rotation slot includes an outer edge and an inner edge with the rotation slot formed thereby in between and further wherein said rotation slot includes at least one pin hole in said outer edge and at least one pin hole in said inner edge; a limit boss in said second curved cup wherein said limit boss is configured to fit within said rotation slot; a rotation slot pin wherein said rotation slot pin is configured to fit within said at least one outer edge pin hole and connect said at least one outer edge pin hole with said at least one inner edge pin hole across said rotation slot and restrict movement of said limit boss within said rotation slot; and
b. connecting said first cup and said second cup to form a first unit and connecting the first unit with a user appendage.

19. The method of claim 18 further including a size adjustment device connected with said cup pin within said cup holes wherein said size adjustment device allows said first curved cup to move axially around said cup pin along multiple axis and front to back and wherein said size adjustment device is a bushing with a center hole wherein said center hole of said bushing is conformed to receive the shaft of said cup pin and wherein said bushing fits within at least one of said cup holes and wherein said bushing is of a certain dimension wherein said certain dimension is selected from a group of dimensions consisting of: the same dimension as at least one of said cup holes and a smaller dimension than at least one of said cup holes.

20. The method of claim 18 further including a rotation plate wherein said rotation plate is connected with said cup pin beneath said cup cap and above the outside surface of said first curved cup.

* * * * *